United States Patent [19]
Faust et al.

[11] Patent Number: 5,241,985
[45] Date of Patent: Sep. 7, 1993

[54] FLOW CONTROL VALVE SYSTEM

[75] Inventors: Valentine T. Faust, Bow; Dean L. Kamen, Bedford, both of N.H.

[73] Assignee: Deka Products Limited Partnership, Manchester, N.H.

[21] Appl. No.: 979,408

[22] Filed: Nov. 19, 1992

Related U.S. Application Data

[63] Continuation of Ser. No. 674,813, Mar. 22, 1991, abandoned, which is a continuation-in-part of Ser. No. 615,612, Nov. 17, 1990, abandoned, and a continuation-in-part of Ser. No. 614,806, Nov. 17, 1990, abandoned, which is a continuation-in-part of Ser. No. 523,801, May 15, 1990, abandoned, and a continuation-in-part of Ser. No. 345,387, May 1, 1989, Pat. No. 4,976,162, which is a continuation-in-part of Ser. No. 92,481, Sep. 3, 1987, Pat. No. 4,826,482, which is a continuation-in-part of Ser. No. 22,167, Mar. 5, 1987, Pat. No. 4,808,161, and a continuation-in-part of Ser. No. 836,023, Mar. 4, 1986, Pat. No. 4,778,451.

[51] Int. Cl.$^5$ .............................................. F16K 31/365
[52] U.S. Cl. .............................. 137/505.13; 137/495; 137/614.14
[58] Field of Search ................ 137/494, 505.13, 513.5, 137/505.41, 495, 614.14; 251/335.2, 61.1

[56] References Cited

U.S. PATENT DOCUMENTS

| | | | |
|---|---|---|---|
| 121,487 | 12/1871 | Burnett ........................ | 251/335.2 X |
| 1,800,995 | 4/1931 | Gaunt et al. ................... | 251/335.2 X |
| 2,141,070 | 12/1938 | Newell .......................... | 251/335.2 X |
| 2,189,750 | 2/1940 | Barge ........................... | 137/505.13 X |
| 2,301,031 | 11/1942 | Ferguson ....................... | 137/505.13 X |
| 2,715,009 | 8/1955 | Beekley ......................... | 251/335.2 X |
| 2,943,643 | 7/1960 | Pinter et al. ................... | 137/513.5 X |
| 3,547,427 | 12/1970 | Kelly et al. .................... | 137/505.41 X |
| 3,648,726 | 3/1972 | Caparone et al. ............... | 137/505.41 |
| 3,730,215 | 5/1973 | Conery et al. .................. | 137/505.13 X |
| 3,948,285 | 4/1976 | Flynn ............................ | 137/505.13 X |
| 4,157,808 | 6/1979 | Eidsmore ....................... | 251/335.2 X |
| 4,300,552 | 11/1981 | Cannon ......................... | 128/214 |
| 4,431,019 | 2/1984 | Kopp et al. ..................... | 137/513.5 X |
| 4,515,588 | 5/1985 | Amendolia ..................... | 604/118 |
| 4,537,387 | 8/1985 | Danby et al. ................... | 251/61.1 X |
| 4,796,660 | 1/1989 | Bron ............................ | 137/504 |
| 4,860,793 | 8/1989 | Härtl ............................ | 251/335.2 X |

FOREIGN PATENT DOCUMENTS

| | | |
|---|---|---|
| 684872 | 11/1939 | Fed. Rep. of Germany ........................ 137/505.41 |
| 1802413 | 6/1969 | Fed. Rep. of Germany . |
| 792708 | 1/1936 | France ........................ 137/505.13 |
| 169 | of 1893 | United Kingdom ........... 137/505.13 |
| 1429932 | 3/1976 | United Kingdom . |

*Primary Examiner*—John Rivell
*Attorney, Agent, or Firm*—Bromberg & Sunstein

[57] ABSTRACT

A valve for controlling intravenous fluid includes a flexible membrane (11), which together with a rigid body (21) forms a valving chamber (29). Two mouths (27, 32) lead into and out of the valving chamber. In one embodiment, a stem (23) having an enlarged portion (15) is attached to the membrane's inner face and extends into the outlet mouth. Fluid pressure on the inner face causes the enlarged portion of the stem to press against a narrower portion (38) of the outlet conduit, thereby preventing flow through the outlet conduit. External pressure on the membrane's outer face causes the enlarged portion of the stem to separate from the outlet conduit's walls, thereby permitting flow through the outlet conduit. In another embodiment, a groove (43) is placed near one of the mouths. The membrane may be pressed against the rigid body and the groove, so as to prevent flow except through the groove and to variably restrict flow through the groove.

8 Claims, 5 Drawing Sheets

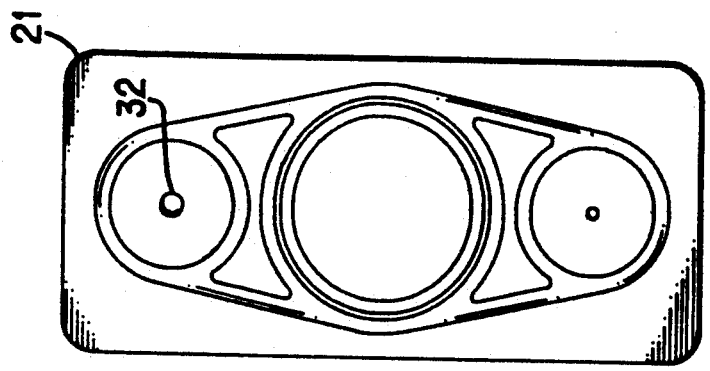
FIG.6
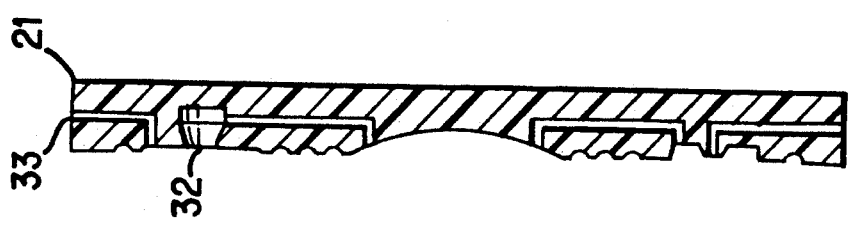
FIG.5
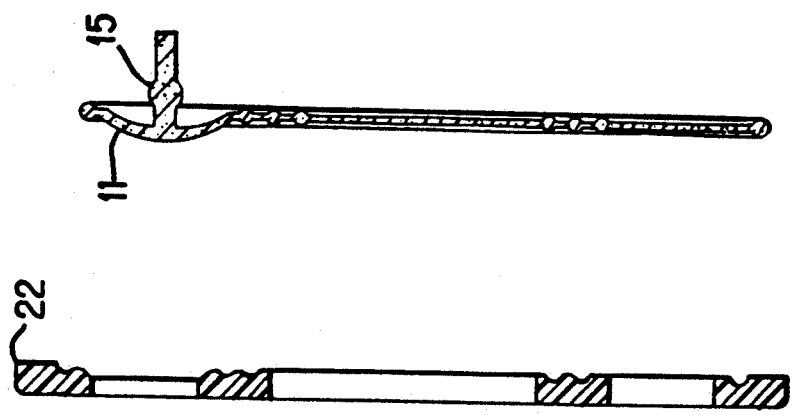
FIG.4
FIG.3
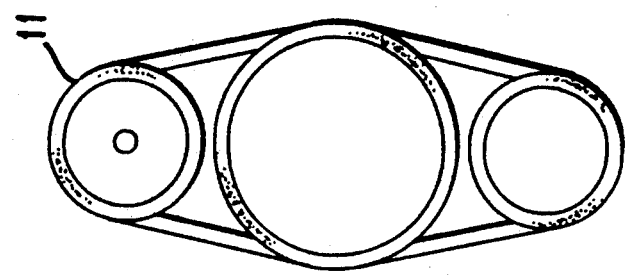
FIG.2

FLOW CONTROL VALVE SYSTEM

This is a continuation of copending application Ser. No. 07/674,813 filed on Mar. 22, 1991 now abandoned which application is a continuation-in-part of applications Ser. No. 615,612 filed Nov. 17, 1990, (for Acoustic Volume Measurement with Fluid Management Capability), now abandoned, and Ser. No. 614,806 filed Nov. 17, 1990 (for Integral Intravenous Fluid Delivery Device; hereinafter the "Spike Application"), now abandoned, which are continuations-in-part of applications Ser. No. 523,801 filed May 15, 1990 (for a Valve System with Removable Fluid Interface; hereinafter the "Valve Application") now abandoned, and Ser. No. 345,387 filed May 1, 1989, issued Dec. 11, 1990 as U.S. Pat. No. 4,976,162 (for an Enhanced Pressure Measurement Flow Control System; hereinafter the "System Application"), which is a continuation-in-part of application Ser. No. 092,481 filed Sep. 3, 1987, issued as U.S. Pat. No. 4,826,482, which is a continuation-in-part of applications Ser. No. 022,167 filed Mar. 5, 1987, issued as U.S. Pat. No. 4,808,161, and Ser. No. 836,023 filed Mar. 4, 1986, issued as U.S. Pat. No. 4,778,451. These related applications are hereby incorporated herein by reference.

TECHNICAL FIELD

The present invention relates generally to systems for controlling, and in particular to medical infusion technology, although other embodiments are possible.

SUMMARY OF THE INVENTION

The present invention provides for a valve system for controlling the flow of fluid, particularly an intravenous fluid. The valve system is designed such that the portion of the valve that comes in contact with the fluid may be disposed, and the rest of the system may be reused without being sterilized.

In one embodiment the present invention provides a valve that remains normally closed. The valve may be opened when inserted in a central unit, which can carefully control the amount of fluid being delivered through the line. Thus, when the disposable portion of valve system is removed from the central control unit, the valve automatically closes, thereby preventing additional fluid from flowing. This valve includes a body and a flexible membrane. The outer edge of the flexible membrane is attached to the body, so as to form a fluid chamber between the membrane and body. The body has two mouths which are in communication with the fluid chamber. The input mouth provides fluid communication between the chamber and the line, typically an intravenous line which in turn would be connected to an intravenous fluid supply. The output mouth leads to an output conduit providing fluid communication between the fluid chamber and a line, which is typically connected to the patient receiving the intravenous fluid. The membrane has attached thereto a stem, which preferably is integral with the flexible membrane. The stem passes through the fluid chamber and the fluid conduit. At the end of the stem is an enlarged end functioning as a stopper. The stopper normally prevents fluid flow through the output conduit. The output conduit has two different diameters; the smaller diameter is located closer to the output mouth, and the wider diameter is located further from the output mouth. The smaller diameter is smaller than the diameter of the stopper, but larger than the diameter of the rest of the stem. The larger output conduit diameter is larger than the diameter of the stopper. Thus, the stem can move back and forth through the output conduit; however, the stopper cannot normally pass through the narrow portion of the output conduit.

In this valve the stopper is normally pulled towards the narrow portion of the conduit by the springiness of the membrane. When the pressure in the fluid chamber increases, the membrane is forced away from the output mouth, tending to pull to the stem and the stopper along with it. The stopper is thus further urged against the narrow portion of the output conduit, thereby preventing the flow of fluid through the output conduit even as the pressure in the fluid chamber increases. When this valve is mounted in the appropriate control unit, an actuator or air pressure can force the membrane towards the output mouth and, in turn, cause the stopper to move away from the narrow portion of the output conduit towards the wider portion of the output conduit, thereby permitting the flow of fluid through the output conduit. The actuator can further press the membrane towards the output mouth and seal the membrane against the output mouth, thereby preventing the flow of fluid through the output conduit.

An alternative embodiment of the invention also includes a flexible membrane which is attached along its outer edge to a body. The body has input and output mouths and a groove disposed adjacent to the output mouth. As the membrane is urged towards the output mouth, fluid flow is forced through a groove. The membrane should have sufficient thickness so that, as additional force is exerted on the outer face of the membrane, the inner face of the membrane bulges into the groove and further restricts the flow of fluid therethrough. Sufficient force may be applied to the outer face of the membrane so that the bulge of the membrane completely fills the groove, thereby preventing fluid flow through the conduit.

In another embodiment of the invention the portion of the body forming the fluid chamber comprises a curved wall that curves from the outer edge of the membrane towards the output mouth, such that the wall is convex with respect to the membrane. The input mouth is located on the curved wall between the outer edge of the membrane and the output mouth, so as the membrane is urged towards the output mouth the membrane variably restricts flow through the first mouth.

BRIEF DESCRIPTION OF THE DRAWINGS

FIG. 2 shows a plan view of a membrane that is used in a device having two valves and a pressure chamber.

FIG. 3 shows a rigid member of the device in which the membrane of FIG. 2 is used.

FIG. 4 shows a cross section of the membrane of FIG. 2.

FIG. 5 shows a cross section of another rigid member of the device that uses the components shown in FIG. 2 and FIG. 3.

FIG. 6 shows a plan view of the member shown in FIG. 5.

DESCRIPTION OF SPECIFIC EMBODIMENTS

Figure 1:
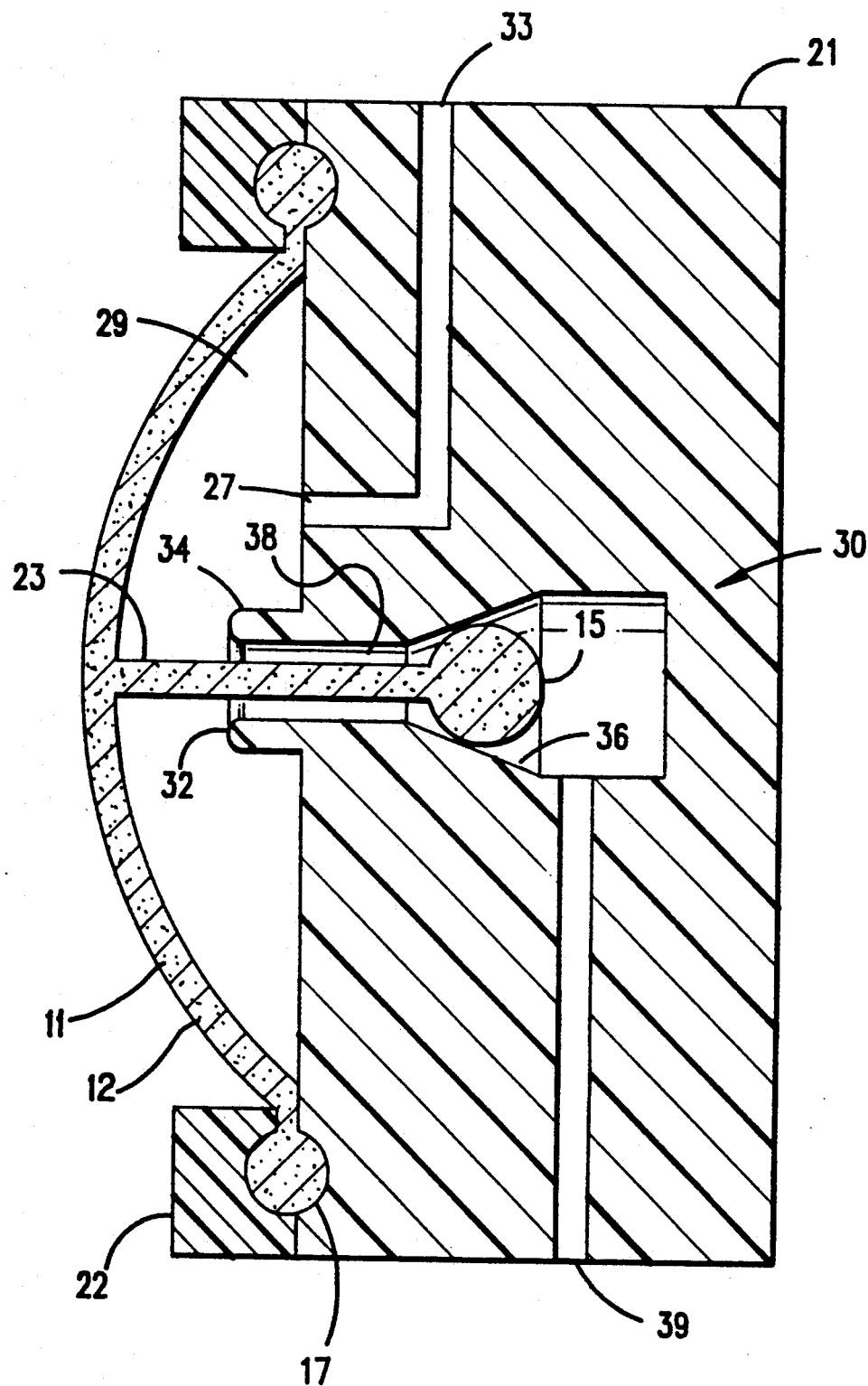
FIG. 1 shows a cross section of a valve that is used with a central unit and that is normally closed.

FIG. 1 shows a cross-section of a valve that may be used with a central unit in order to control the flow of fluid through the valve, and that is normally closed. Fluid flows from port 33, which is connected to a source of fluid, typically intravenous fluid, coming from an intravenous fluid supply through an intravenous line. The fluid passes through the valve to a second port 39, which may be connected to an intravenous line leading to a patient. Fluid flowing from the port 33 through input mouth 27 flows into a fluid chamber 29, which is formed by the membrane 11 and a body 21. The body 21 is made of a relatively rigid material, while membrane 11 is made up of a relatively flexible material. The outer edge of the membrane 11 has an O-ring 17 which is sandwiched between the body 21 and a second rigid member 22, so as to prevent fluid from leaking out around the edges of the membrane 11. Attached to the middle of the membrane 11 is a stem 23, which is preferably made integral to the membrane 11. Disposed in the body 21 is an output conduit 30 connecting the output mouth 32 with the output port 39. The output conduit 30 has at least two sections, a narrow section 38 and an expanded section 36. The diameter of the narrow section 38 is greater than the diameter of the stem 23 but less than the diameter of the stopper 15, whereas the diameter of the expanded section 36 is greater than the diameter of stopper 15. The stem 23 passes through the output mouth 32 and the narrow section 38 of the output conduit. The stem 23 may move back and forth within the narrow section 38 of the output conduit. The stopper 15, however, cannot easily fit through the narrow portion 38. Preferably, the membrane is molded in a curved shape as shown, so that it pulls the stem 23 and the stopper 15, forcing the stopper 15 against the narrow portion 38 of the conduit.

When the input port 33 is connected to fluid supply, fluid enters the chamber 29, usually with some head pressure. This pressure creates a force on the membrane 11, further causing the stopper to be urged against the narrow portion 38 of the output conduit 30. The greater this pressure becomes, the more the stopper 15 is urged against the narrow portion 38. In order to allow flow through the output conduit 30, a force must be applied to the outer face 12 of the membrane 11 to cause the stopper 15 to move away from the narrow portion 38 of the conduit 30, and thereby allow flow through the output conduit 30. The valve may be placed in a central unit that will provide this force, either by a mechanical actuator or a pneumatic system. The actuator may continue to apply force on the membrane 11 so that the membrane is urged against the output mouth 32. In order to enhance the seal between the membrane 11 and the output mouth 32, a protrusion 34 may extend from the body 21. By urging the membrane 11 against the protrusion 34 the control unit can stop flow through the valve.

As just described, the actuator of the central unit is used to set the position of the membrane 11 in order to either permit or restrict flow. Alternatively, a force may be applied on the membrane 11, by means of a spring for instance, so as to cause a fairly constant flow of fluid through the valve. By placing this spring against the membrane 11, the stopper 15 is held away from the narrow section 38 of the output conduit 30. If the pressure of fluid entering the valve through the input port 33 increases, the membrane 11 will be forced further away from the output mouth 32, causing the stopper to approach the narrow portion 38 of the output conduit 30. If the spring is loaded correctly, an increase in the input pressure would increase flow resistance by the stopper 15, without completely stopping flow. If the input pressure were to decrease, the membrane 11 would move closer towards the output mouth 32, causing the stopper 15 to exert less resistance on fluid flowing through the valve. In this way, a fairly constant flow rate through the valve may be maintained.

Figure 8:
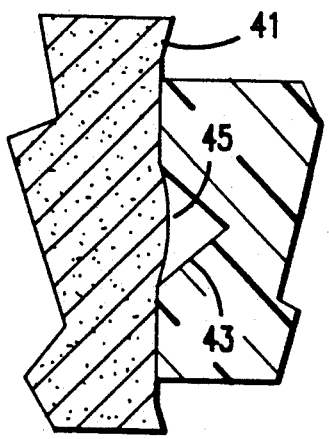
FIG. 8 shows a detail of the protrusion and membrane of the valve shown in FIG. 7.

This valve may be used in lieu of valve A of the disposable housing unit 124 of FIG. 8 of the aforementioned U.S. application Ser. No. 523,801 (the Valve Application). This disposable unit has a pressure conduction chamber and a second valve, valve B, and is used to regulate the flow rate of fluid. Without the normally-closed valve of FIG. 1, the disposable unit shown in the Valve Application would allow fluid to flow therethrough after it has been detached from the central unit. Any flow through the disposable unit after it has been detached from the central unit cannot, of course, be controlled or measured by the central unit. With the normally-closed valve of FIG. 1 of the present application built into the disposable unit, flow is stopped by the normally-closed valve when the disposable unit is removed from the central unit. FIGS. 2-6 show the components of such a disposable unit having a normally-closed valve as valve A. FIG. 2 shows a plan view of the membrane 11, and FIG. 4 shows a cross section of the membrane 11. The membrane 11 is sandwiched between the body 21 shown in cross section in FIG. 5, and a second rigid member 22 shown in cross section FIG. 3. FIG. 6 shows a plan view of the body 21. The membrane 11 is preferably made of silicone and is formed by injection molding. The body 21 shown in FIG. 5 can be made of two pieces each of which may be formed by injection molding. It is easier to construct the internal conduits in the body 21 by forming the body 21 of two pieces.

Figure 7:
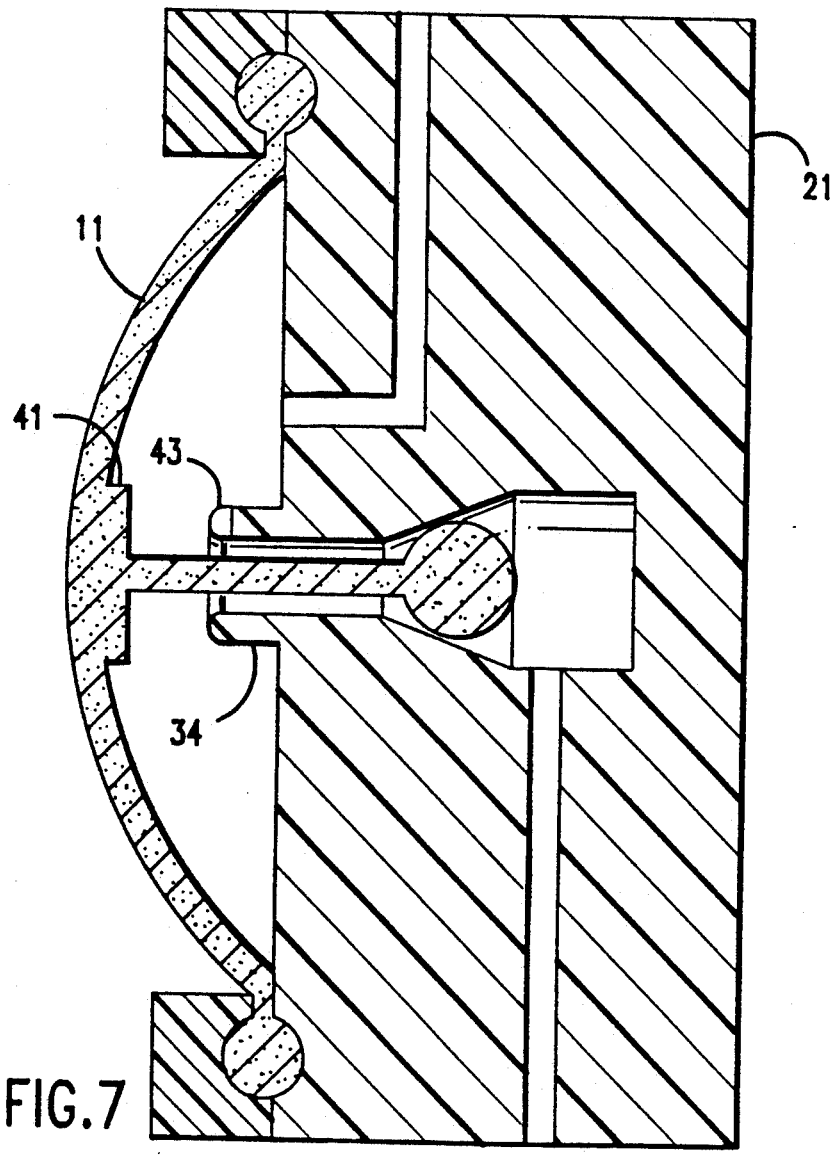
FIG. 7 shows a cross section of another valve according to the invention.

FIG. 7 shows a valve very similar to the valve shown in FIG. 1. In the valve of FIG. 7 the protrusion 34 has a V-shaped notch 43 disposed therein. The membrane 11 of this valve has a thickened portion 41. The membrane 11 may be urged towards the body 21 of the valve by means of a mechanical actuator or pressurized gas, so that the thickened portion 41 of the membrane 11 is urged against the protrusion 34. Further force on the outer face of the membrane 11 will cause the thickened portion 41 of membrane 11 to bulge into the notch 43, as shown in FIG. 8. In FIG. 8 the bulge 45 protrudes into the notch 43. As additional force is applied to the outer face of the membrane 11, the bulge 45 increases in size, and thereby further limits the flow through notch 43. With sufficient force the bulge 45 may completely block the notch 43 and prevent any flow through the valve. The stopper 15 shown in FIG. 7 performs the same way as the stopper shown in FIG. 1, that is the stopper 15 prevents flow from the fluid chamber through the output unless some force is applied to the outer face of the membrane 11, which is preferably done by an actuator of a control unit.

Figure 9:
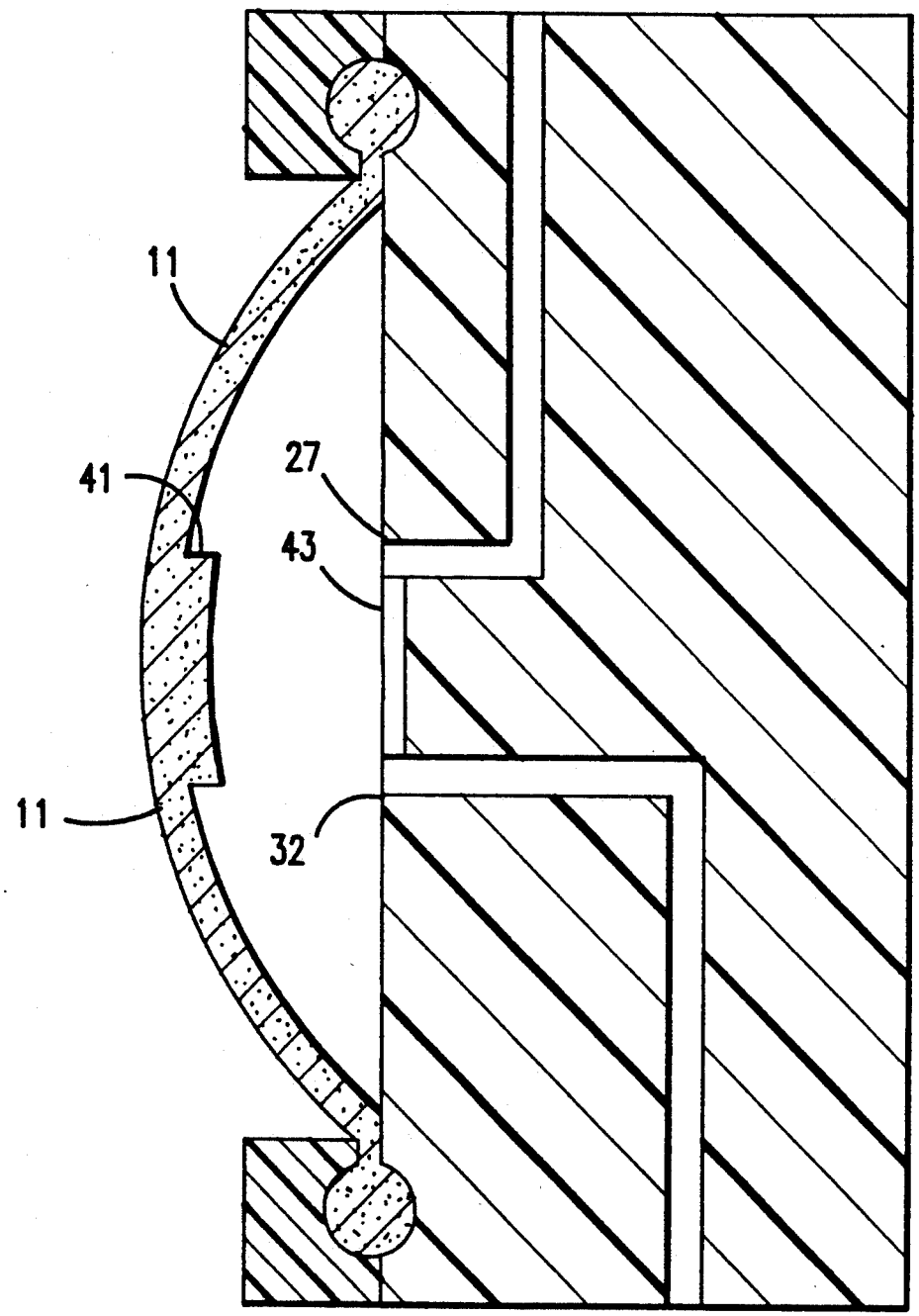
FIG. 9 shows a cross section of another valve having a notch disposed in the body thereof.

FIG. 9 shows alternative to the valve of FIG. 7. The valve of FIG. 9 does not have a protrusion nor a stopper. The notch 43 is disposed between the input mouth 27 and the output mouth 32. As in the valves shown in FIGS. 1 and 7 the membrane 11 is urged towards the output mouth 32. When the thickened portion 41 of the membrane 11 comes into contact with the body 21, all fluid flowing through the valve must essentially flow through the notch 43, thereby restricting the fluid flow. Additional pressure on the membrane 11 can cause the membrane to bulge into the notch 43, further restricting the flow through the valve. Sufficient pressure on the membrane 11 will cause the membrane to completely fill the notch 43.

Figure 10:
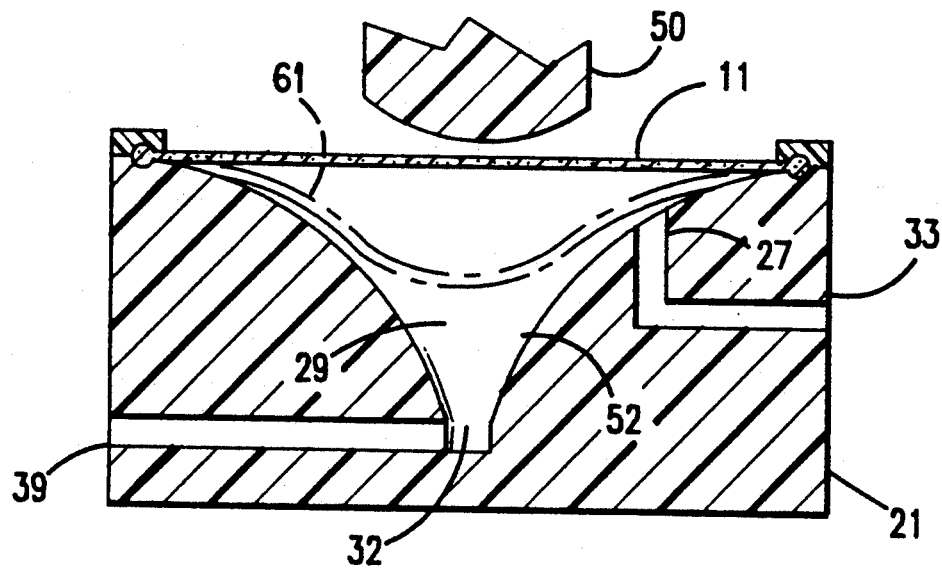
FIG. 10 shows a cross section of a valve having curved walls, which is used to precisely control the flow of fluid therethrough.
Figure 11:
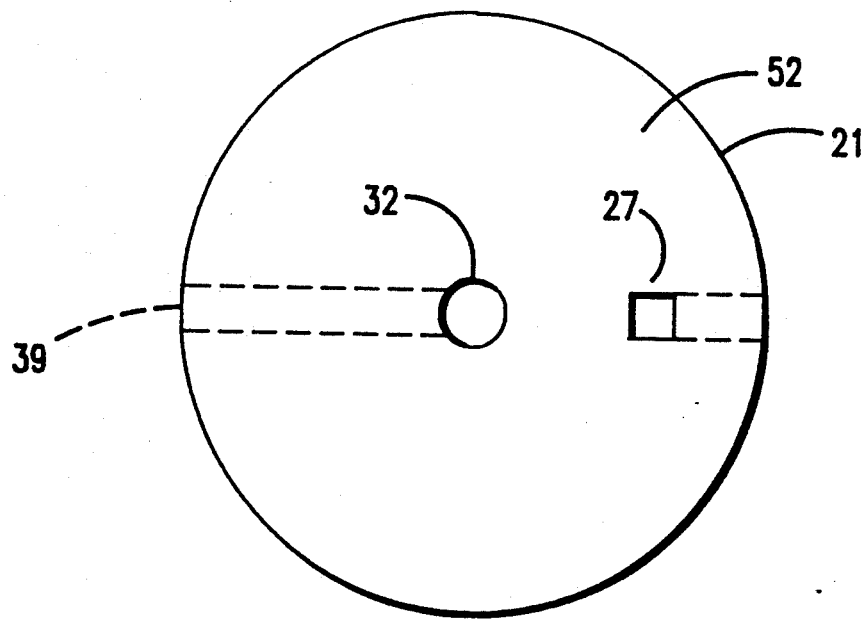
FIG. 11 shows a top plan view of the body of the valve shown in FIG. 10.

FIG. 10 shows a cross section of another valve for precisely controlling the fluid flow. In this embodiment, the chamber 29 has a curved wall 52. From the perspective of the membrane 11, which is of course attached at its outer edge to the body, the wall 52 is convex. As the mechanical actuator 50 forces the membrane 11 towards the output mouth 32 (as shown by dashed lines 61), the membrane 11 restricts flow of fluid through the shaped aperture 27, which is connected to the input port 33. The further the mechanical actuator 50 depresses the membrane 11, the greater the membrane 11 restricts flow from the aperture 27. The membrane 11 may be sufficiently urged against the wall 52 to stop flow through the valve altogether. In lieu of a mechanical actuator 50, pneumatic means may be used for urging the membrane 11 towards the output mouth 32. FIG. 11 shows a top plan view of the body 21 of the valve shown in FIG. 10. It can be seen from this view that the aperture 27 is rectangular. This shape is preferred for better flow control.

The valve of FIG. 10 may be combined with the stem/stopper structure of the valve shown in FIG. 1. A stem may be attached to the center of the membrane 11, and an expanding output conduit as shown in FIG. 1 may be placed below the output mouth 32. The stem would pass through the output mouth 32 and the stopper would be located in the expanded portion of the output conduit. Unless the membrane 11 is depressed by the actuator 50, the stopper would be urged against the output mouth 32, but, when the actuator 50 urges the membrane down, the stopper would be forced away from the output mouth thereby permitting flow through the output mouth 32.

What is claimed is:

1. A disposable valve unit comprising:
   a body forming at least one wall of an open fluid chamber and having an input conduit leading to the fluid chamber and an output conduit leading from an output mouth on the fluid chamber, the output mouth including a smaller cross section than an enlarged portion of the output conduit;
   a flexible membrane having an inner face and an outer face, said membrane being attached to said body so as to enclose the open fluid chamber of said body such that said flexible membrane is responsive to fluid pressure imposed by fluid entering the fluid chamber through the input conduit and said membrane being sufficiently flexible such that it can be depressed across the chamber and into contact with the output mouth; and
   a stem, attached to said flexible membrane, having a narrow portion narrower than the output mouth inserted through the output mouth and having an enlarged portion sitting within the enlarged portion of the output conduit so that movement of said flexible membrane in response to pressure on the outer face or fluid pressure against the inner face moves the enlarged portion of said stem with respect to the smaller cross section of the output mouth to regulate the flow of fluid through the output conduit.

2. The disposable valve unit of claim 1 wherein said stem and said flexible membrane are integrally formed of a single material.

3. The disposable valve unit of claim 1 wherein said stem is sufficiently short so that when there is no pressure difference across said membrane the enlarged portion of said stem is pulled by said membrane against the smaller cross section of the output mouth to prevent flow of fluid through the output conduit.

4. The disposable valve unit of claim 2 wherein said stem is sufficiently short so that when there is no pressure difference across said membrane the enlarged portion of said stem is pulled by said membrane against the smaller cross section of the output mouth to prevent flow of fluid through the output conduit.

5. The disposable valve unit of claim 1 wherein said membrane has a substantially thick portion adjacent to said stem so that when said membrane is urged towards the output mouth the substantially thick portion restricts the flow of fluid into the output mouth.

6. The disposable valve unit of claim 2 wherein said membrane has a substantially thick portion adjacent to said stem so that when said membrane is urged towards the output mouth the substantially thick portion restricts the flow of fluid into the output mouth.

7. The disposable valve unit of claim 5 wherein said body further includes a groove disposed therein adjacent to the output mouth so that fluid may flow through the groove into the output conduit, so that when said membrane is urged towards the output mouth, the substantially thick portion of said membrane tends to fill the groove and restrict the flow of fluid through the groove.

8. The disposable valve unit of claim 6 wherein said body further includes a groove disposed therein adjacent to the output mouth so that fluid may flow through the groove into the output conduit, so that when said membrane is urged towards the output mouth, the substantially thick portion of said membrane tends to fill the groove and restrict the flow of fluid through the groove.

* * * * *